(12) United States Patent
Peterson

(10) Patent No.: US 6,447,489 B1
(45) Date of Patent: *Sep. 10, 2002

(54) LAPAROSCOPIC ACCESS TOOL WITH GAS SEAL

(75) Inventor: Francis C. Peterson, Prescott, WI (US)

(73) Assignee: Ethicon Endo-Surgey, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/483,880

(22) Filed: Jan. 18, 2000

(51) Int. Cl.$^7$ .................................................. A61M 5/00
(52) U.S. Cl. .................. 604/264; 604/167.06; 606/192; 600/204; 600/207
(58) Field of Search ........................ 604/23, 27, 164.01, 604/104, 163, 164.02, 164.08, 246, 256, 264, 34, 35, 30, 167.01, 162, 537, 167.02, 167.03, 167.04, 167.06, 331, 349, 337–339, 341–344, 346, 347; 606/192, 172, 191; 600/32, 31, 204–208, 235, 114–116

(56) References Cited

U.S. PATENT DOCUMENTS

| | | | |
|---|---|---|---|
| 4,760,933 A | | 8/1988 | Christner et al. |
| 4,828,554 A | | 5/1989 | Griffin |
| 5,127,626 A | | 7/1992 | Hilal et al. |
| 5,158,553 A | | 10/1992 | Berry et al. |
| 5,217,001 A | * | 6/1993 | Nakao et al. .................. 128/4 |
| 5,295,994 A | * | 3/1994 | Bonutti .......................... 604/192 |
| 5,330,437 A | | 7/1994 | Durman |
| 5,364,372 A | | 11/1994 | Danks et al. |
| 5,441,485 A | * | 8/1995 | Peters .......................... 604/101 |
| 5,538,509 A | | 7/1996 | Dunlap et al. |
| 5,545,150 A | | 8/1996 | Danks et al. |
| 5,545,179 A | * | 8/1996 | Williamson, IV ........... 606/213 |
| 5,549,625 A | * | 8/1996 | Bircoll ......................... 606/192 |
| 5,580,344 A | | 12/1996 | Hasson |
| 5,593,418 A | * | 1/1997 | Mollenauer .................. 606/192 |
| 5,634,911 A | | 6/1997 | Hermann et al. |
| 5,634,937 A | | 6/1997 | Mollenauer et al. |
| 5,662,615 A | | 9/1997 | Blake, III |
| 5,681,342 A | * | 10/1997 | Benchetrit .................... 606/192 |
| 5,720,730 A | | 2/1998 | Blake, III |
| 5,730,748 A | * | 3/1998 | Fogarty et al. .............. 606/159 |
| 5,746,720 A | | 5/1998 | Stouder, Jr. |
| 5,882,344 A | | 3/1999 | Stouder, Jr. |
| 5,897,533 A | * | 4/1999 | Glickman .................... 604/256 |
| 5,941,860 A | * | 8/1999 | Wheeler ....................... 604/327 |
| 5,967,970 A | | 10/1999 | Cowan et al. |
| 5,997,515 A | * | 12/1999 | de la Torre .................. 604/256 |
| 6,004,303 A | * | 12/1999 | Peterson ...................... 604/264 |
| 6,090,088 A | * | 7/2000 | Nichols ........................ 604/347 |
| 6,171,282 B1 | * | 1/2001 | Ragsdale ..................... 604/171 |
| 6,171,299 B1 | * | 1/2001 | Bonutti ........................... 606/1 |
| 6,197,002 B1 | * | 3/2001 | Peterson ................... 604/164.01 |
| 6,240,924 B1 | * | 6/2001 | Fogarty et al. .............. 128/892 |

FOREIGN PATENT DOCUMENTS

| | | |
|---|---|---|
| GB | 2 275 420 | 8/1994 |
| WO | WO 94/22357 | 10/1994 |
| WO | WO 98 48724 | 11/1998 |
| WO | WO 99 29242 | 6/1999 |

* cited by examiner

Primary Examiner—Brian L. Casler
Assistant Examiner—Cris Rodriguez
(74) Attorney, Agent, or Firm—Dean Garner

(57) ABSTRACT

A laparoscopic access apparatus enabling the removal of tissue or other debris from a surgical site. A catheter having a longitudinal access is provided with a flexible internal sleeve having distal and proximal ends. The sleeve forms an inner channel through which laparoscopic surgical instruments may be passed. The sleeve is mounted with axial tautness along one side of the catheter, it is provided with a loose, baggy portion elsewhere in the catheter defining an inflatable cavity between the catheter and sleeve. A gas port is positioned to enable gas under pressure from a body cavity to enter the inflatable cavity adjacent the distal end thereof to thereby collapse the sleeve and seal the channel.

16 Claims, 3 Drawing Sheets

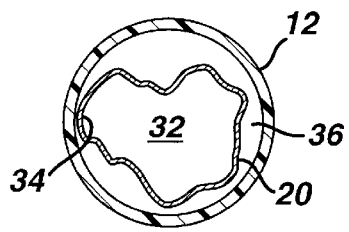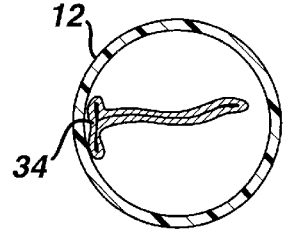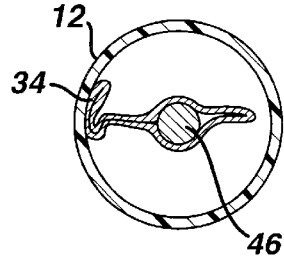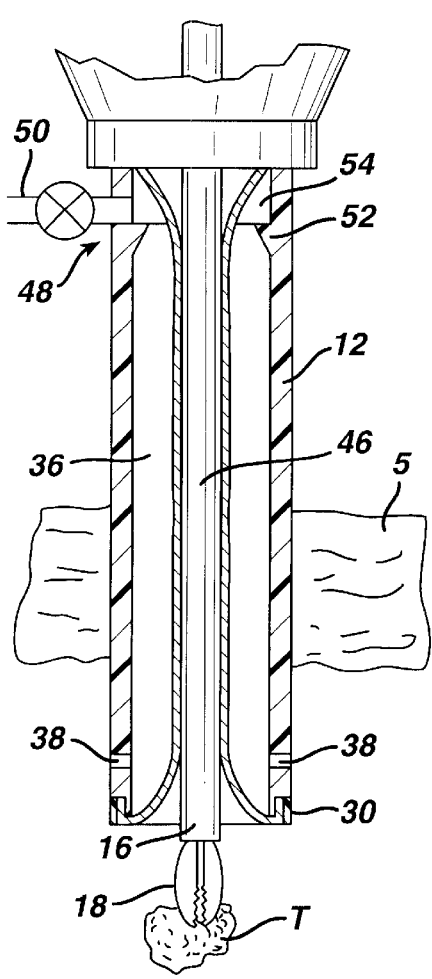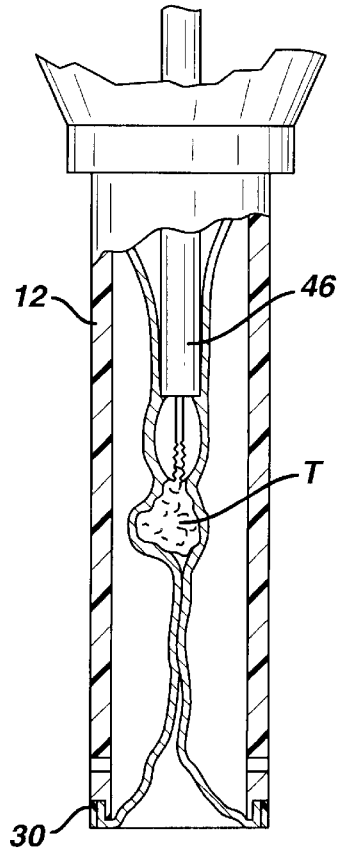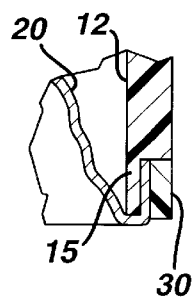

LAPAROSCOPIC ACCESS TOOL WITH GAS SEAL

FIELD OF THE INVENTION

The invention relates to apparatus useful in laparoscopic surgery, and particularly to a device enabling tissue to be withdrawn from a body cavity using laparoscopic surgical tools while maintaining gas pressure within the body cavity.

BACKGROUND OF THE INVENTION

Laparoscopic surgery commonly requires that one or more small openings be made through the tissues of a patient to enable the insertion of laparoscopic surgical instruments. Commonly, the body cavity (the abdomen, the knee capsule, etc.) in which laparoscopic surgery is to be performed is first inflated with a gas such as $CO_2$ to provide an open, inflated area within which the surgical instruments may be manipulated. A catheter may be provided through the tissue wall bounding the body cavity, and it is through the catheter that the surgical instruments are introduced into the body cavity. Because the body cavity is pressurized, there is a tendency for the pressurizing gas within the body cavity to escape outwardly through the catheter, thereby deflating the cavity. To counter this problem, a number of devices have been proposed to provide a pressure seal within the catheter, but yet enable laparoscopic instruments to be passed inwardly and outwardly of the body cavity through the catheter. One such seal is shown in Mollenauer, et al., U.S. Pat. No. 5,634,937. Another is shown in published UK Patent Application GB 2 275 420 (Gaunt, et al.), and yet another is shown in PCT International Publication No. WO 94/22357 (Yoon). The sealing devices described in the above references by and large relate to inflatable, donut-like devices, through the center of which laparoscopic instruments may be passed.

Although those portions of laparoscopic instruments that are introduced through a cannula into a body cavity are routinely fairly uniform in size, and thus can be introduced and withdrawn from the catheter with some ease, a problem arises when instruments with diameters much larger or smaller that usual are to be introduced into the body cavity, or particularly when pieces of tissue are severed within the body cavity and are to be withdrawn through the catheter without significant loss of pressure in the body cavity. Particularly in the latter case, the tissue sample may not easily fit through the gas seal that is provided, and in this instance, the tissue sample may in fact have to be painstakingly severed into small pieces in order to be successfully removed. If a large tissue sample is removed with some force, then the seal mechanism may be damaged, resulting in a loss of pressure within the body cavity with easily foreseeable medical problems.

It would be desirable to provide a laparoscopic access apparatus that would maintain a seal against the escape of gas from within a body cavity, that would enable large tissue samples to be withdrawn through the catheter without damage to the pressure seal, and that would also adapt to a variety of instrument sizes and configurations that are to be passed into and out of the catheter.

BRIEF DESCRIPTION OF THE INVENTION

I have found that a suitable gas seal may be made from a film of generally tubular flexible material carried in laparoscopic access catheter, the film at one side of the catheter being stretched tautly, and the film elsewhere in the catheter remaining baggy and loose. The outer surface of the baggy film portion defines, with the catheter walls, an inflatable cavity between the catheter and the sleeve, and the inner surface of the sleeve defines a channel leading through the catheter. The sleeve is joined at its distal and proximal ends to the catheter adjacent its distal and proximal ends.

The taut configuration of the flexible sleeve on one side of the catheter, together with the loose, baggy nature of the sleeve elsewhere in the catheter and the sealing of the sleeve at its ends to the catheter, enable the baggy portion of the sleeve to readily deform toward the catheter walls without ripping or tearing to allow passage through the channel of large objects such as tissue specimens from within a body cavity within which laparoscopic surgery occurs. The apparatus includes a gas port positioned to enable gas under pressure from within the body cavity to enter the cavity between the sleeve and catheter to thereby collapse the sleeve and seal the channel defined by the sleeve.

In its sealed configuration, the sleeve will readily accept the passage of laparoscopic instruments passed through the catheter into the body cavity, the sleeve collapsing onto and conforming to the instruments to maintain the gas seal. As large tissue specimens are removed through the catheter, the sleeve will similarly collapse about the tissue specimen, such that as the specimen is drawn outwardly, the channel within the sleeve will enlarge to accept the specimen, the sleeve collapsing against itself beneath the specimen as the specimen passes to thereby maintain the gas seal.

Thus, in one embodiment, the invention provides a laparoscopic access apparatus enabling the removal of tissue or other debris from a surgical site. The apparatus comprises a catheter having a longitudinal axis. A flexible sleeve having distal and proximal ends is carried within the catheter, the sleeve forming an inner channel through which laparoscopic surgical instruments may be passed. The sleeve is mounted with axial tautness along one side of the catheter, and has a loose, baggy portion elsewhere in the catheter defining an inflatable cavity between the catheter and sleeve. The apparatus includes a gas port positioned to enable gas under pressure to enter the cavity adjacent to the distal end of the sleeve to thereby collapse the sleeve and seal the channel.

BRIEF DESCRIPTION OF THE DRAWING

FIG. 8 is a cross-sectional view taken along line 8—8 of FIG. 4 and showing the flexible sleeve in an open configuration;

FIG. 9 is a view similar to that of FIG. 8 but showing the flexible sleeve in a sealed configuration;

FIG. 10 is a view similar to that of FIGS. 8 and 9, but showing the flexible sleeve in a sealed, collapsed position about the shaft of a laparoscopic instrument;

FIG. 11 is a broken-away view, in partial cross-section, showing a step in the removal of a tissue specimen through the apparatus, and further showing a gas supply system;

FIG. 12 is a view similar to that of FIG. 11, showing another step in the tissue removal procedure; and FIG. 13 is a broken-away, cross-sectional view of the structure designated 13 in FIG. 1.

BRIEF DESCRIPTION OF THE PREFERRED EMBODIMENT

Figure 1:
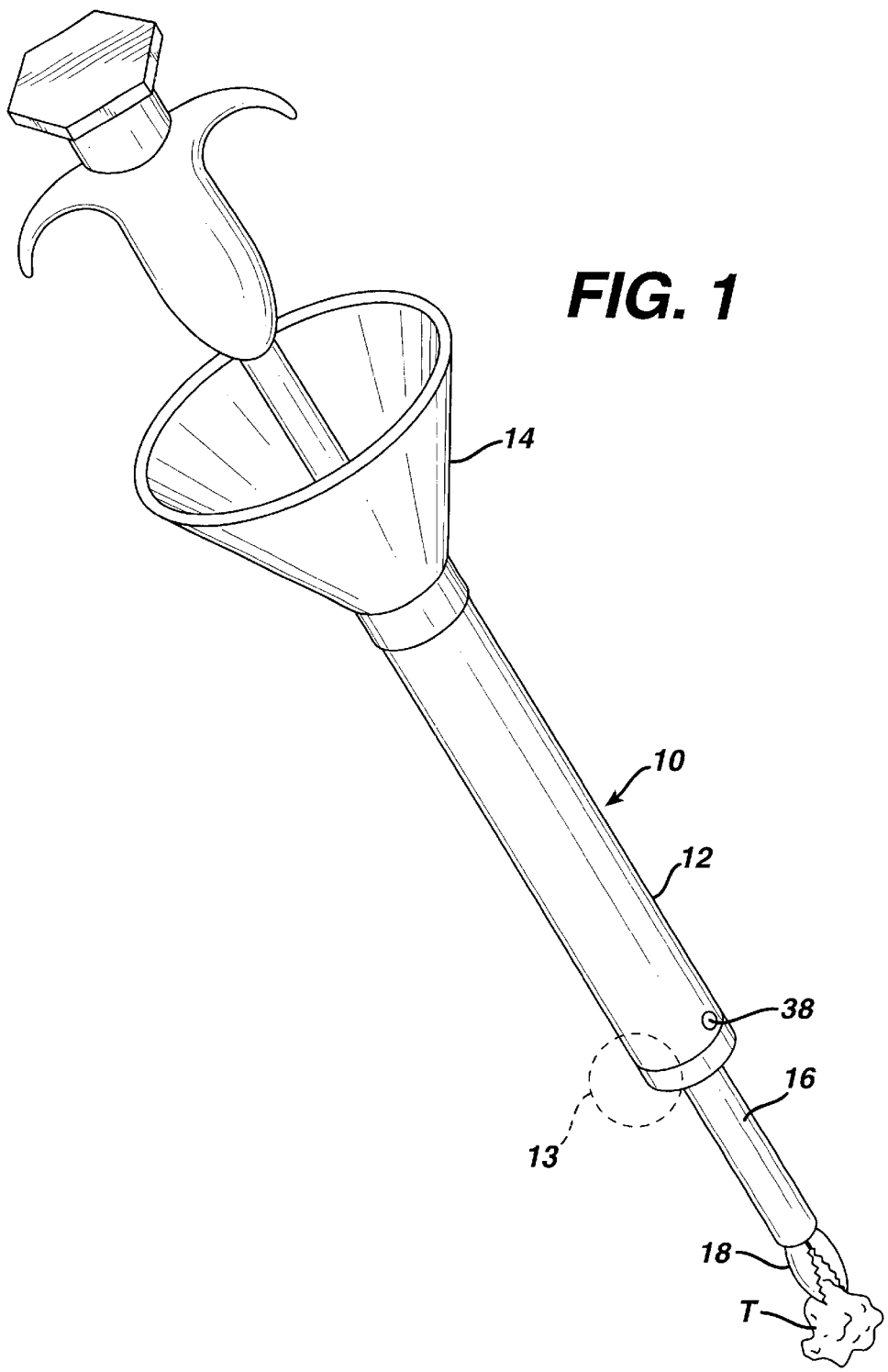
FIG. 1 is a perspective view of an apparatus of the invention.

Referring first to FIG. 1, the laparoscopic access apparatus of the invention is labeled generally as 10 and includes an elongated catheter 12 which desirably is rigid and which may be made from any suitable material such as a metal or plastic material. At its outer, or proximal end, the catheter may have mounted to it a cup shaped or funnel shaped entrance portion 14 for the purpose of enabling laparoscopic tools to be easily introduced by a surgeon into the catheter from outside the body cavity. A laparoscopic tool is typified in FIG. 1 as a forceps 16, the forceps having jaws 18 illustrated as clamping to an enlarged tissue specimen "T" that is to be removed through the catheter. As shown, the tissue specimen approaches the size of the catheter 12.

Figure 4:
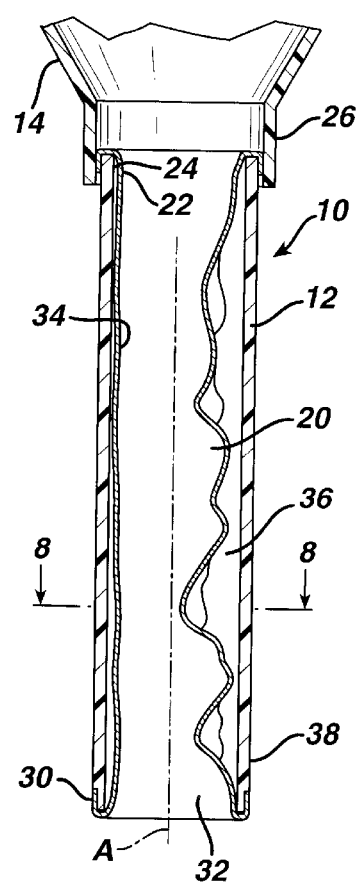
FIG. 4 is a broken-away, cross-sectional view of an apparatus of the invention.

The catheter 12 is shown perhaps best in FIG. 4. The catheter is tubular, and commonly is made of a rigid plastic material such as polyethylene, polycarbonate or polysulfone. A funnel shaped portion 14 is illustrated as being carried at the top (the proximal end) of the catheter, and serves simply to direct laparoscopic tools into the catheter. Within the catheter is a flexible sleeve 20, of generally tubular design, the sleeve having a proximal end portion 22 that is doubled back over the proximal mouth 24 of the catheter. In the depicted embodiment, the funnel shaped portion 14 has a lower, generally cylindrical neck section 26 that fits tightly over the double-backed portion of the sleeve 20 to secure the proximal end of the sleeve to the proximal end of the catheter. An adhesive or cement can be employed as desired to secure the cylindrical neck 26 and doubled-back portion of the sleeve to the proximal end of the catheter.

Figure 2:
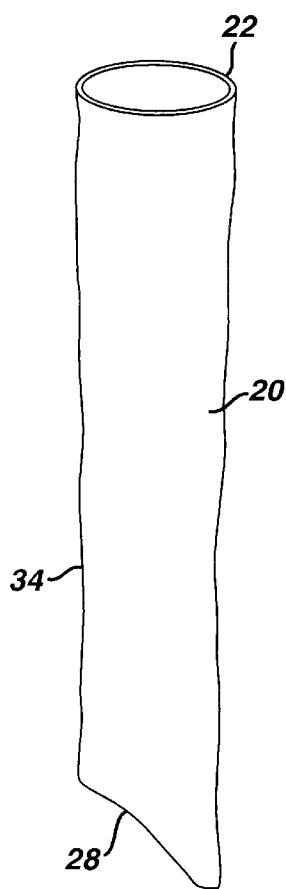
FIG. 2 is a perspective view of a flexible sleeve used in the apparatus in FIG. 1.
Figure 3:
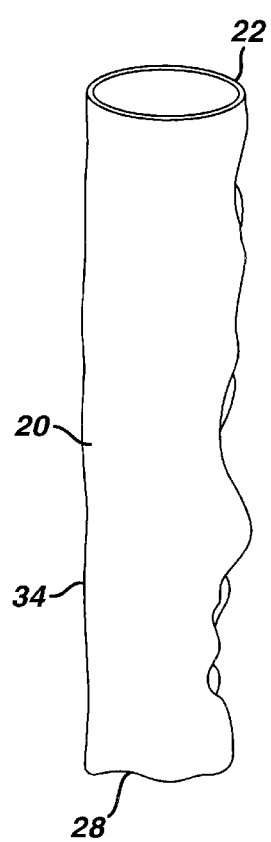
FIG. 3 is a perspective view of the sleeve in FIG. 2, showing a loose, baggy feature of the sleeve.

Referring to FIG. 2, a section of sleeve is depicted having its proximal end 22 at generally right angles to its length, but having its bottom or distal end 28 portion cut at a sharp angle to its length, e.g., at an angle of about 40 degrees to the length of the sheath. When the distal end 28 of the sheath is raised so as to be substantially at right angles to the length of the sheath, as shown in FIG. 3, the sheath itself becomes loose and baggy.

The distal end 28 of the sheath is similarly doubled back about the distal mouth of the catheter, as shown in FIG. 4, and is there attached to the catheter by any appropriate means, a surrounding plastic band 30 being typified in the drawing. An adhesive may be used in place of the band, or in combination with the band, to secure the distal end of the sheath peripherally to the distal end of the catheter. Details of a preferred attachment of the distal end of the sheath to the catheter is shown in FIG. 13. The distal end of the catheter terminates in a short section 15 of reduced diameter and receives the doubled-back portion of the sheath. Band 30 is then received over the doubled back portion of the sheath, the band having an outer diameter that is equivalent to the outer diameter of the catheter proximally of the section 30. In this manner, the catheter and band, as a unit, present a smooth outer surface of uniform diameter to enable the catheter to be received through a tissue wall and into a body cavity.

Sheath 20 is made of a very flexible material, and polyurethane films have given good results. In the preferred embodiment, the film is elastic, although non-elastic films may also be used. The film is in any event sufficiently limp as to readily conform to the shape of the solid object in which it is brought into contact. Sheath 20 itself defines a channel 32 extending within the catheter, and the inner surface of the sheath that faces that the channel is slippery. Slipperiness may be attained either by choosing a sheath material that is normally quite slippery, or by treating the inner surface of the sheath with a material that confers slipperiness. For example, the sheath may be of polyurethane to which a thin film of a fluorocarbon polymer such as poly (tetrefluoroethylene) is bonded, or the sheath may be coated with a hydrophilic material which, when wet, becomes slippery. If desired, a lubricating agent such as a fine biocompatable powder or a lubricating liquid such as a jelly may be applied to the inner surface of the sheath to increase its slipperiness.

Desirably, the sheath has an outer diameter which is somewhat greater than the inner diameter of the catheter, and this, coupled with the baggy nature of the sleeve discussed above, results in the sleeve retaining a baggy configuration within the catheter as shown in FIG. 4. Although bagginess may be obtained by the method described above, other methods may be used to provide bagginess as well. For example, the sleeve may be formed about a mandrel configured to provide the desired baggy configuration. As another example, the sleeve, after having been formed, may simply be stretched in certain areas to provide the desired configuration, the sleeve in this situation desirably being stretchy but not elastic, so that it retains its stretched-out configuration.

As shown best in FIG. 4, one side of the sleeve 34 is pulled taut between its attachments to the catheter. This side of the sheath is the short side shown in FIG. 2. "Taut" as used herein reflects the fact that the side 34 of the sheath does not loosely bag out into the interior of the catheter, but rather maintains a position at or fairly close to the side wall of the catheter. The portion 34 of the sheath need not be actually tight or under axial tension. If desired, the side 34 of the sheath may be actually adhered to the confronting surface of the catheter, as by welding or through the use of an adhesive.

Figure 5:
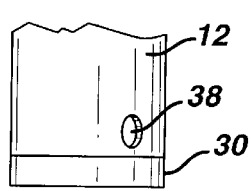
FIG. 5 is a broken-away side view of an apparatus of the invention, showing a gas access port.
Figure 6:
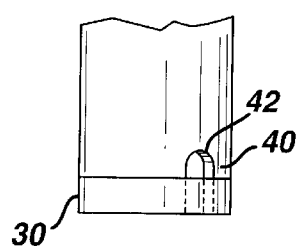
FIG. 6 is a view similar to that of FIG. 5 but showing a different gas access port.
Figure 7:
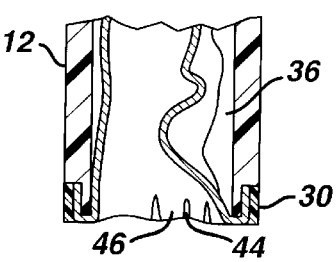
FIG. 7 is a broken-away, cross-sectional view of an apparatus showing a modification of gas access ports.

It will be noted in FIG. 4 that the baggy portion of the sheath 20 defines, with the confronting wall of the catheter, an inflatable cavity 36. A gas port is provided to enable gas from within the body cavity to enter the inflatable space 36 and to collapse the sheath inwardly. A suitable port is shown at 38 in FIGS. 4 and 5 as being formed through the thickness of the catheter wall adjacent the distal end of the catheter; that is, just above the band 30. A variety of gas entry ports can be employed. FIG. 6 shows a generally U-shaped slot 42 formed in the distal end 40 of the catheter, the slot extending proximally of the band 30 far enough so that its proximal portion is open to gas from the body cavity. In FIG. 7, the distal end portion 28 of the sheath is provided with axially extending cuts or slots 44, the slots forming ports through which gas can enter the cavity 36. If desired, the distal end of the sheath can be thus cut or slotted around its periphery to form a plurality of distally extending fingers 46, each finger then being secured to the catheter adjacent its distal end.

FIG. 8 is a cross-sectional view taken along line 8—8 of FIG. 4, and shows the sheath 20 in an open position loosely bounding the channel 32. Once the catheter has been deployed with its distal end portion within a pressurized body cavity, gas under pressure is received through the gas port 38 to inflate the cavity 36, causing the inner walls of the catheter to collapse upon each other to seal the channel 32. This configuration is illustrated in FIG. 9. If the shaft of a laparoscopic instrument, such as the forceps shown in FIGS. 1, 11 and 12, extends through the channel 32, then the inner walls of the sheath collapse about the shaft as shown in FIG. 10, again sealing the channel 32. Inasmuch as the inner surface of the sheath is quite slippery, as discussed above, the gas seal is maintained as the laparoscopic tool is moved proximally or distally or otherwise maneuvered within the sheath as may be necessary during laparoscopic surgery. It will be understood that the sheath is sufficiently baggy as to enable it, when the cavity 36 is inflated, to completely collapse towards the center of the catheter and thereby seal the channel 32.

FIGS. 11 and 12 show steps in a procedure in which a large tissue specimen T is withdrawn through an access apparatus of the invention. In FIG. 11, the catheter 12 is shown in place with its distal end within the body cavity and its proximal end extending outwardly of the body cavity. For ease of visualization, a layer of skin and muscle, representing a wall of a body cavity, is shown generally as S in FIG. 11. Placement of the access catheter through the wall involves the use of a sharpened, solid trocar (not shown) that is inserted within the channel 32 with its sharpened end projecting distally. The body cavity is inflated by means of a suitable needle and gas delivery tubing in a known fashion, and the trocar pierces the layer of skin and muscle S, carrying with it the distal end of the catheter. The trocar (not shown) is then removed, the sheath collapsing as typified in FIG. 9 to seal the channel 32, as described above.

If desired, the catheter may be provided with a gas transport system, as shown at 48 in FIG. 11, comprising a valved gas tube 50 communicating with the catheter adjacent its proximal end. Within the catheter, a peripheral shoulder 52 extends inwardly slightly from the catheter walls to define a circumferential gas channel 54, the shoulder restraining the sheath from collapsing outwardly against the walls of the catheter at this location. Gas from the delivery tube thus may flow distally within the inflatable cavity 36, and thence through the gas port 38 and into the body cavity. The gas tube 50 may also be used to depressurize the proximal end of the inflatable cavity as a very large tissue section is being withdrawn through the catheter, and also may serve to depressurize the body cavity when it is appropriate to do this in a surgical procedure.

In FIGS. 11 and 12, the cannula is shown rotated 90 degrees in a clockwise direction from the positions shown in FIGS. 4, 8, 9 and 10. In FIG. 11, as part of a laparoscopic surgical procedure, a large tissue sample T has been severed from the body within the body cavity and is shown grasped by the jaws 18 of a forceps. The tissue sample must now be withdrawn by the forceps proximally through the channel 32 without significant loss of pressurizing gas within the body cavity. In FIG. 11, it will be seen that the inner walls of the sheath have collapsed against the shaft 46 of the forceps due to inflation of the space 36 between the walls of the catheter and the sheath. As the forceps is withdrawn proximally, the walls of the sheath yield as needed to accept and enfold the tissue sample T, as shown in FIG. 12, such that as the tissue sample proceeds proximally through the channel 32, the walls of the sheath close distally behind the tissue sample to maintain the gas seal.

While several forms of the invention have been shown and described, other forms will be apparent to those skilled in the art. The embodiment shown on the drawings and described above are merely for illustrative purposes and are not intended to limit the scope of the invention, which is defined by the claims which follow.

I claim:

1. Laparoscopic access apparatus enabling the removal of tissue or other debris from a surgical site, comprising a catheter having a longitudinal axis, a flexible sleeve having distal and proximal ends and carried within the catheter, the sleeve forming an inner channel through which laparoscopic surgical instruments may be passed, the sleeve being mounted with axial tautness along one side of the catheter and having a loose, baggy portion defining an inflatable cavity between the catheter and sleeve, the apparatus including a gas port positioned to enable gas under pressure to enter said cavity adjacent said distal end to thereby collapse said sleeve and seal said channel.

2. The apparatus of claim 1 wherein the portion of the sleeve mounted with axial tautness is adhered to the catheter.

3. The apparatus of claim 1 wherein the proximal end of the sleeve is sealed about its periphery to the periphery of the catheter adjacent its proximal end.

4. The apparatus of claim 1 or claim 3 wherein the distal end of the sleeve is mounted to the periphery of the catheter adjacent its distal end.

5. The apparatus of claim 4 wherein said port comprises an aperture through said catheter adjacent the distal end of the catheter.

6. The apparatus of claim 4 wherein said port comprises an aperture formed through said sleeve adjacent the distal end of the catheter.

7. The apparatus of claim 1 wherein said sleeve is formed of a non-elastic material.

8. The apparatus of claim 1 wherein said sleeve is formed of an elastic material.

9. The apparatus of claim 1 wherein said sleeve has an inner surface facing the channel, and including a slippery coating carried by said inner surface.

10. The apparatus of claim 9 wherein said slippery coating is a lubricating liquid.

11. The apparatus of claim 9 wherein said slippery coating is a lubricating powder.

12. The apparatus of claim 9 wherein said slippery coating comprises a film of a fluorocarbon polymer.

13. Laparoscopic access apparatus enabling the removal of tissue or other debris from a surgical site, comprising a catheter having a longitudinal axis, a flexible sleeve having distal and proximal ends and carried within the catheter, the sleeve forming an inner channel through which laparoscopic surgical instruments may be passed, the sleeve being mounted with axial tautness along one side of the catheter and having a loose, baggy portion defining an inflatable cavity between the catheter and sleeve, the apparatus including a gas port positioned to enable gas under pressure to enter said cavity adjacent said distal end to thereby collapse said sleeve and seal said channel, and said sleeve having an inner surface facing the channel, and including a slippery coating carried by said inner surface.

14. The apparatus of claim 13 wherein said slippery coating is a lubricating liquid.

15. The apparatus of claim 13 wherein said slippery coating is a lubricating powder.

16. The apparatus of claim 13 wherein said slippery coating comprises a film of a fluorocarbon polymer.

* * * * *